US011223974B2

(12) United States Patent
Kubo et al.

(10) Patent No.: US 11,223,974 B2
(45) Date of Patent: Jan. 11, 2022

(54) DATA TRANSMISSION APPARATUS AND DATA RECEPTION APPARATUS

(71) Applicants: OMRON HEALTHCARE CO., LTD., Muko (JP); OMRON Corporation, Kyoto (JP)

(72) Inventors: Nobuo Kubo, Kyoto (JP); Toru Deno, Kyoto (JP); Hideki Kondo, Kyoto (JP)

(73) Assignees: OMRON HEALTHCARE CO., LTD., Kyoto (JP); OMRON CORPORATION, Kyoto (JP)

( * ) Notice: Subject to any disclaimer, the term of this patent is extended or adjusted under 35 U.S.C. 154(b) by 128 days.

(21) Appl. No.: 16/733,264

(22) Filed: Jan. 3, 2020

(65) Prior Publication Data

US 2020/0145880 A1    May 7, 2020

Related U.S. Application Data

(63) Continuation of application No. PCT/JP2018/028823, filed on Aug. 1, 2018.

(30) Foreign Application Priority Data

Aug. 9, 2017   (JP) .............................. JP2017-154761

(51) Int. Cl.
*H04W 4/00* (2018.01)
*H04W 28/06* (2009.01)
(Continued)

(52) U.S. Cl.
CPC ....... *H04W 28/065* (2013.01); *A61B 5/02225* (2013.01); *H04W 4/38* (2018.02);
(Continued)

(58) Field of Classification Search
CPC ....... H04W 28/065; H04W 4/80; H04W 4/38; H04W 76/14; H04W 52/24; H04W 84/10;
(Continued)

(56) References Cited

U.S. PATENT DOCUMENTS

| 7,486,700 B2 * | 2/2009 | Miyazaki ................ H04L 69/04 370/477 |
| 7,583,701 B2 * | 9/2009 | Miyazaki .............. H04L 69/168 370/477 |

(Continued)

FOREIGN PATENT DOCUMENTS

| JP | 2004-187326 A | 7/2004 |
| JP | 5852620 B2 | 2/2016 |

(Continued)

OTHER PUBLICATIONS

Official Communication issued in International Patent Application No. PCT/JP2018/028823, dated Oct. 2, 2018.

(Continued)

*Primary Examiner* — Marceau Milord
(74) *Attorney, Agent, or Firm* — Keating and Bennett, LLP

(57) ABSTRACT

According to the first aspect of the present invention, a data transmission apparatus includes a transmission control unit which generates a packet for one-way communication including first difference sensor data, and a transmission unit which transmits the generated packet. The first difference sensor data is a difference between first sensor data measured by a sensor and a reference value associated with the first sensor data.

7 Claims, 9 Drawing Sheets

(51) Int. Cl.
*H04W 4/38* (2018.01)
*H04W 76/14* (2018.01)
*H04W 4/80* (2018.01)
*A61B 5/022* (2006.01)
*H04W 8/00* (2009.01)
*H04W 52/24* (2009.01)
*H04W 84/10* (2009.01)
*H04W 84/18* (2009.01)

(52) U.S. Cl.
CPC ............ *H04W 4/80* (2018.02); *H04W 8/005* (2013.01); *H04W 52/24* (2013.01); *H04W 76/14* (2018.02); *H04W 84/10* (2013.01); *H04W 84/18* (2013.01)

(58) Field of Classification Search
CPC ..... H04W 84/18; H04W 28/06; H04W 5/022; H04W 8/00
USPC ................. 370/329, 342, 509, 335, 320
See application file for complete search history.

(56) References Cited

U.S. PATENT DOCUMENTS

| | | | | |
|---|---|---|---|---|
| 8,475,479 | B2* | 7/2013 | Linsi ................. | A61F 9/007 606/167 |
| 8,774,017 | B2* | 7/2014 | Miyazaki ............. | H04L 69/161 370/252 |
| 9,268,725 | B2 | 2/2016 | Shiraishi ............... | H04L 69/22 |
| 9,974,492 | B1* | 5/2018 | Dicks .................... | G16H 40/63 |
| 10,388,411 | B1* | 8/2019 | Dicks .................... | A61B 5/0022 |
| 10,478,127 | B2* | 11/2019 | Sampson ............... | A61B 5/0022 |
| 10,560,135 | B1* | 2/2020 | Dicks .................... | G06Q 20/405 |
| 2004/0125817 | A1* | 7/2004 | Miyazaki ............... | H04W 28/06 370/411 |
| 2013/0137378 | A1* | 5/2013 | Folden ................. | H04W 52/245 455/67.11 |
| 2014/0237595 | A1* | 8/2014 | Sridhara ................ | G06F 21/55 726/23 |
| 2015/0036514 | A1* | 2/2015 | Zhu ..................... | H04W 52/244 370/252 |
| 2015/0366518 | A1* | 12/2015 | Sampson ............. | A61B 5/0261 600/301 |
| 2016/0029149 | A1* | 1/2016 | Morikawa ............. | H04W 76/14 455/41.2 |
| 2016/0080372 | A1* | 3/2016 | Martin .................. | H04W 12/50 713/168 |
| 2017/0206046 | A1* | 7/2017 | Shimazawa ............... | G06F 3/14 |
| 2017/0228502 | A1* | 8/2017 | Rickard ................ | G16H 10/60 |
| 2017/0281000 | A1* | 10/2017 | Wedekind ............ | A61B 5/0022 |
| 2018/0001184 | A1* | 1/2018 | Tran ....................... | G06F 1/163 |
| 2018/0083884 | A1* | 3/2018 | Kuang ................ | H04L 49/9005 |
| 2018/0103859 | A1* | 4/2018 | Provenzano ............ | A61B 5/681 |
| 2018/0182491 | A1* | 6/2018 | Belliveau ............ | A61B 5/0004 |
| 2018/0338709 | A1* | 11/2018 | Krans .................. | A61B 5/0022 |
| 2019/0324436 | A1* | 10/2019 | Cella ..................... | G06N 7/005 |
| 2021/0186385 | A1* | 6/2021 | Wedekind .............. | H04L 69/18 |

FOREIGN PATENT DOCUMENTS

| | | |
|---|---|---|
| JP | 2017-041770 A | 2/2017 |
| JP | 2017-129979 A | 7/2017 |

OTHER PUBLICATIONS

English translation of Official Communication issued in International Patent Application No. PCT/JP2018/028823, dated Feb. 13, 2020.

* cited by examiner

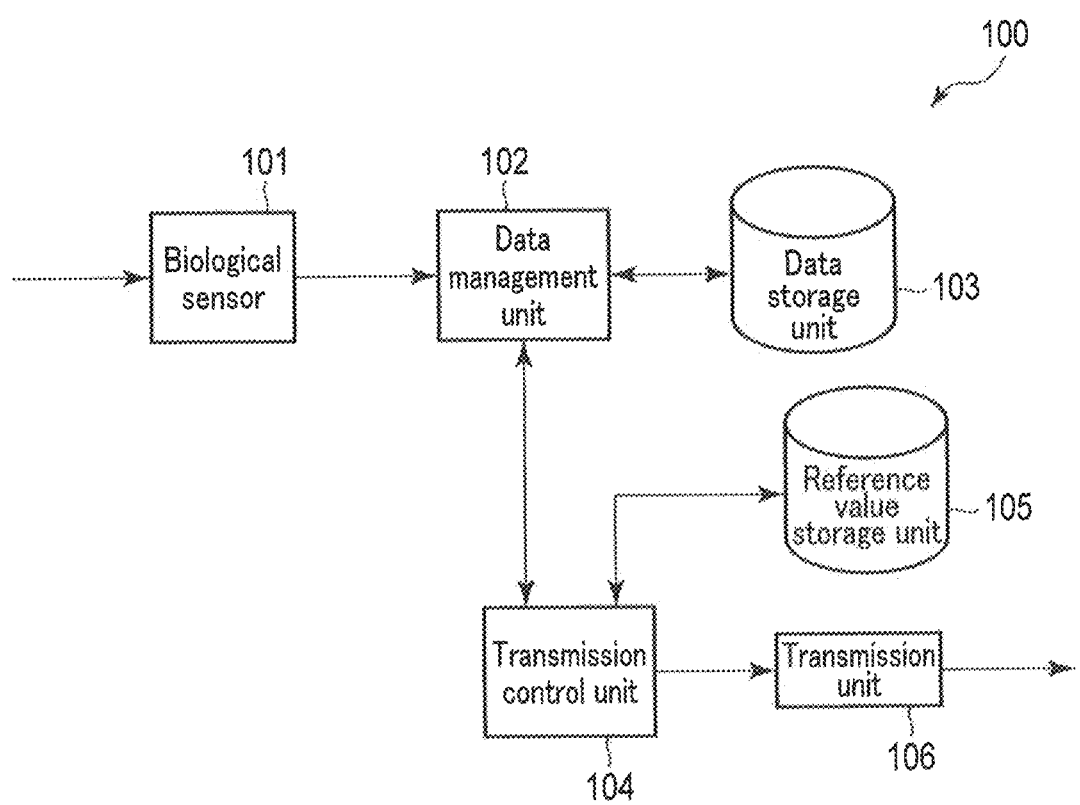
F I G. 1
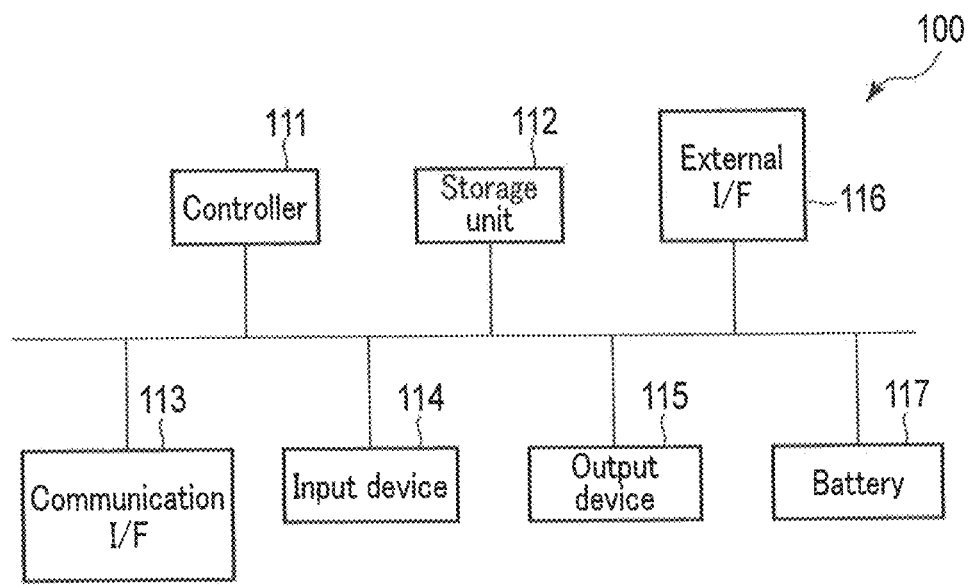
F I G. 2

| ID | Time | DifSys | DifDia | DifPulse |
|---|---|---|---|---|

FIG. 8

| ID | Baseline | Time | DifSys | DifDia | DifPulse |
|---|---|---|---|---|---|

FIG. 9

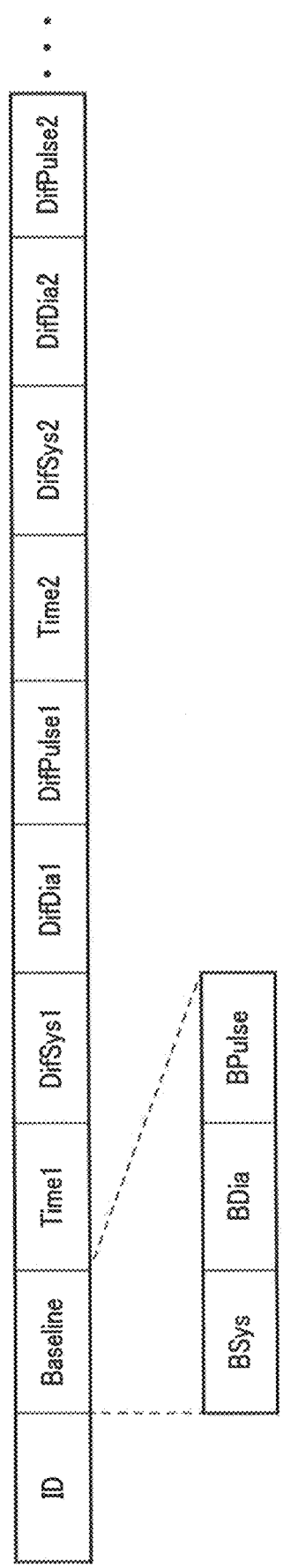
F I G. 10

FIG. 11

| Data No. | SYS | DIA | PULSE |
|---|---|---|---|
| 1 | 135 | 85 | 72 |
| 2 | 120 | 75 | 90 |
| 3 | 115 | 90 | 78 |
| 4 | 105 | 80 | 60 |
| 5 | 112 | 72 | 66 |

FIG. 12

| SYS difference | DIA difference | PULSE difference |
|---|---|---|
| 30 | 13 | 12 |
| 15 | 3 | 30 |
| 10 | 18 | 18 |
| 0 | 8 | 0 |
| 7 | 0 | 6 |

FIG. 13

| Number of measurements | For measurement value transmission | For difference transmission | Data reduction rate |
|---|---|---|---|
| 5 sets' worth | 120 bit | 99 bit | 18 % |
| 6 sets' worth | 144 bit | 114 bit | 21 % |
| 7 sets' worth | 168 bit | 129 bit | 23 % |
| 8 sets' worth | 192 bit | 144 bit | 25 % |
| 9 sets' worth | 216 bit | 159 bit | 26 % |
| 10 sets' worth | 240 bit | 174 bit | 28 % |
| 11 sets' worth | 264 bit | 189 bit | 28 % |
| 12 sets' worth | 288 bit | 204 bit | 29 % |
| 13 sets' worth | 312 bit | 219 bit | 30 % |
| 14 sets' worth | 336 bit | 234 bit | 30 % |

DATA TRANSMISSION APPARATUS AND DATA RECEPTION APPARATUS

CROSS-REFERENCE TO RELATED APPLICATIONS

This application is a Continuation Application of PCT Application No. PCT/JP2018/028823, filed Aug. 1, 2018 and based upon and claiming the benefit of priority from Japanese Patent Application No. 2017-154761, filed Aug. 9, 2017, the entire contents of all of which are incorporated herein by reference.

FIELD

The present invention relates generally to data transmission and reception by one-way communication.

BACKGROUND

A blood pressure monitor with a function of transmitting blood pressure data to a smartphone of a user is on the market. When such a function is used, the user may be able to view its own blood pressure measurement result via a smartphone at various circumstances. A short-range wireless communication technique, more specifically, Bluetooth (trademark registered) technique, is typically used for the transmission of blood pressure data. Generally, Bluetooth communication (connection) is achieved on a smaller scale and with greater power-saving compared to WLAN (Wireless Local Area Network) communication. Bluetooth specification version 4.0 is also called BLE (Bluetooth Low Energy), and is characterized by its superior power-saving capabilities compared with prior specifications.

The BLE connection has its problems such as the complicated nature of the pairing operation to be performed by the user, the complicated nature of the communication procedures after pairing, the smartphone needing to support BLE, the blood pressure monitor (and smartphone) needing high-performance hardware (processor, memory), the development/evaluation cost being high, the size of communication overhead being large, and the non-suitability for small capacity data transmission.

On the other hand, BLE may perform one-way communication called advertising. Japanese Patent No. 5852620 discloses the technique of transmitting option data by including it in a vacant area of the data field of the advertisement packet. If the blood pressure data is transmitted using advertising, the pairing operation and the complex communication procedures after pairing becomes unnecessary, and the above problems may be largely solved.

SUMMARY

However, with one-way communication, the data transmission apparatus cannot verify if transmitted data has been successfully received by the data reception apparatus. Thus, the data transmission apparatus must be able to practically perform retransmission of data, assuming a lack of the data in the data reception apparatus. Downsizing the capacity of transmission data is desired in order to compensate for the reduced transmission efficiency associated with data retransmission.

In a first aspect of the present invention, the data transmission apparatus includes a transmission control unit configured to generate a first packet for one-way communication including first difference sensor data, and a transmission unit configured to transmit the generated first packet, the first difference sensor data being a difference between first sensor data measured by a sensor and a reference value associated with the first sensor data. Typically, it is rare for the biological information of the same person such as the blood pressure to drastically change over a short period; thus, the number of bits allocated for transmission of the difference sensor data may be limited compared to the number of bits allocated for transmission of raw sensor data. Hence, according to the data transmission apparatus of this aspect, the packet transmitted by one-way communication may be made to a smaller capacity.

In an second aspect of the present invention, the transmission control unit is configured to generate the first packet without storing the reference value in the first packet. Thus, the sensor data may be securely transmitted by substantial encryption.

In a third aspect of the present invention, the transmission control unit is configured to generate the first packet to further include an identifier indicative of the reference value being one of a plurality of preset reference values determined in advance. According to this aspect, the data reception apparatus uses correspondence between the identifier and the preset reference value to specify the preset reference value indicated by the identifier stored in the packet, and reliably restores the sensor data. Further, even if a third party intercepts this packet, the original sensor data may not be restored as long as the third party does not know the correspondence between the identifier and the preset reference value. In other words, the sensor data may be securely transmitted by substantial encryption.

In a fourth aspect of the present invention, the transmission control unit is configured to generate the first packet to further include the reference value and second difference sensor data, and the second difference sensor data is a difference between second sensor data and the reference value, the second sensor data being measured by the sensor and different from the first sensor data. According to this aspect, the reference value itself is stored in the same packet as the first difference sensor data and the second difference sensor data generated using the reference value. Thus, the data reception apparatus may reliably restore the sensor data.

In a fifth aspect of the present invention, the transmission control unit is configured to generate the first packet to further include the reference value, and the reference value is second sensor data measured by the sensor and different from the first sensor data. According to this aspect, similar to the fourth aspect, the reference value itself is stored in the same packet as the first difference sensor data generated using the reference value. Thus, the data reception apparatus may reliably restore the sensor data. Furthermore, according to this aspect, using the second sensor data as the reference value may lead to downsizing of the capacity by as much as the second difference sensor data compared to the fourth aspect.

According to a sixth aspect of the present invention, the transmission control unit is configured to generate a second packet for one-way communication including the first sensor data, instead of generating the first packet when a data size of the first difference sensor data is larger than a data size of the first sensor data, and the transmission unit is configured to transmit the generated second packet. Thus, according to this aspect, the effect of reducing capacity by transmitting the first packet may be clearly achieved.

According to a seventh aspect of the present invention, the first sensor data is biological data. Thus, the biological data, such as blood pressure data, may be transmitted with high efficiency.

According to an eighth aspect of the present invention, the data reception apparatus includes a reception unit configured to receive a first packet for one-way communication including first difference sensor data, and a restoring unit configured to restore first sensor data, which is a base of the first difference sensor data, by adding the first difference sensor data included in the received first packet to a reference value associated with the first difference sensor data, the first difference sensor data being a difference between the first sensor data and the reference value. Typically, it is rare for the biological information of the same person such as the blood pressure to drastically change over a short period; thus, the number of bits allocated for transmission of the difference sensor data may be limited compared to the number of bits allocated for transmission of raw sensor data. Hence, according to the data reception apparatus, the capacity of the packet transmitted by the one-way communication may be reduced.

According to a ninth aspect of the present invention, in the data reception apparatus, the first packet is without the reference value, and the restoring unit is configured to determine the reference value based on reception data other than the first packet or based on user input. Thus, the sensor data may be securely transmitted by substantial encryption.

According to a tenth aspect of the present application, a storage unit configured to store a plurality of preset reference values is further included, the first packet further includes an identifier indicative of the reference value being one of the preset reference values, and the restoring unit is configured to restore the first sensor data by selecting a preset reference value indicated by the identifier included in the received first packet from the preset reference values, and adding the first difference sensor data included in the received first packet to the selected preset reference value. Hence, the data reception apparatus uses correspondence between the identifier and the preset reference value to specify the preset reference value indicated by the identifier stored in the packet, and reliably restores the sensor data. Further, even if a third party intercepts this packet, the original sensor data may not be restored as long as the third party does not know the correspondence between the identifier and the preset reference value. In other words, the sensor data may be securely transmitted by substantial encryption.

According to an eleventh aspect of the present invention, the first packet further includes the reference value and second difference sensor data, the restoring unit is configured to restore second sensor data, which is a base of the second difference sensor data, by adding the second difference sensor data included in the received first packet to the reference value included in the received first packet, and the second difference sensor data is a difference between the second sensor data and the reference value. According to this aspect, the reference value itself is stored in the same packet as the first difference sensor data and the second difference sensor data generated using the reference value. Thus, the data reception apparatus may reliably restore the sensor data.

According to a twelfth aspect of the present invention, the first packet further includes the reference value, the reference value is second sensor data different from the first sensor data, and the restoring unit is configured to restore the first sensor data by adding the first difference sensor data to the second sensor data. According to this aspect, the reference value itself is stored in the same packet as the first difference sensor data generated using the reference value, which is similar to the tenth aspect. Thus, the data reception apparatus may reliably restore the sensor data. Furthermore, according to this aspect, using the second sensor data as the reference value may lead to downsizing of the capacity by as much as the second difference sensor data compared to the tenth aspect.

According to a thirteenth aspect of the present invention, the first sensor data is biological data. Thus, the biological data, such as blood pressure data, may be transmitted with high efficiency.

The present invention can reduce the capacity of the packet transmitted by one-way communication.

BRIEF DESCRIPTION OF THE DRAWINGS

FIG. 1 is a block diagram showing an application example of a data transmission apparatus according to an embodiment.

FIG. 2 is a block diagram showing a hardware configuration of a data transmission apparatus according to an embodiment.

FIG. 8 is a diagram showing a first example of a data configuration for storage in a payload of a PDU field of a packet transmitted by a data transmission apparatus according to an embodiment.

FIG. 9 is a diagram showing a second example of a data configuration for storage in a payload of a PDU field of a packet transmitted by a data transmission apparatus according to an embodiment.

FIG. 10 is a diagram showing a third example of a data configuration for storage in a payload of a PDU field of a packet transmitted by a data transmission apparatus according to an embodiment.

FIG. 11 is a diagram showing five sets of sensor data.

FIG. 12 is a diagram showing difference sensor data corresponding to the sensor data of FIG. 11.

FIG. 13 is a diagram illustrating a capacity reduction effect when the difference sensor data of FIG. 12 is transmitted using the data configuration of FIG. 10.

DETAILED DESCRIPTION

Figure 3:
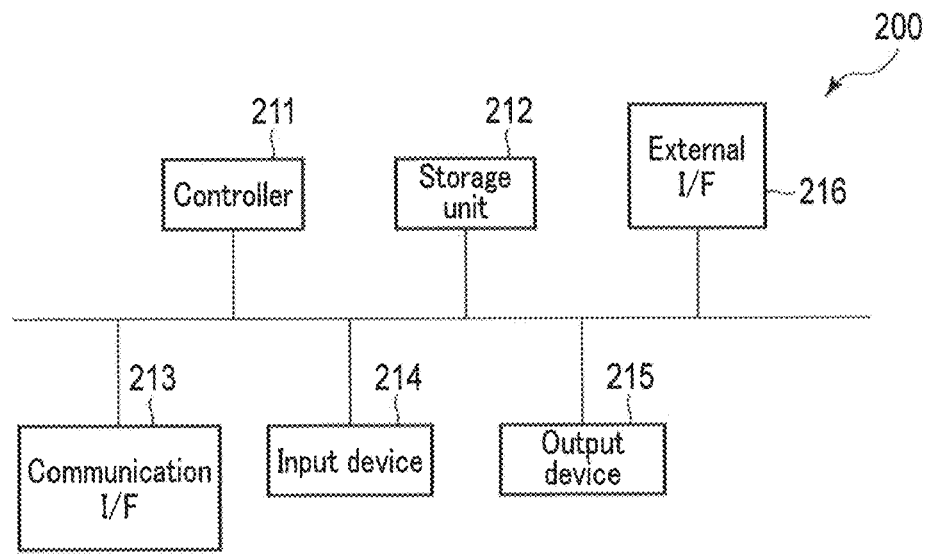
FIG. 3 is a block diagram showing a hardware configuration of a data reception apparatus according to an embodiment.

Hereinafter, a certain embodiment (hereinafter referred to as the "present embodiment") according to one aspect of the present invention will be described in detail with reference to the accompanying drawings.

Furthermore, elements which are the same or similar to the explained elements will be denoted with the same or similar symbols, and overlapping explanations will be basically omitted.

§ 1 Application Example

First, one example of an application of the present invention will be described with reference to FIG. 1. FIG. 1 schematically shows an application example of a data transmission apparatus 100 according to the present embodiment. The data transmission apparatus 100 includes at least a biological sensor 101, a data management unit 102, a data storage unit 103, a transmission control unit 104, a reference value storage unit 105, and a transmission unit 106.

The biological sensor 101 obtains biological data by measuring an amount related to biological information of a user. The biological sensor 101 sends the biological data to the data management unit 102. The data management unit 102 receives the biological data from the biological sensor 101 and writes the same to the data storage unit 103. The data storage unit 103 may be subjected to read and write operations by the data management unit 102 for sensor data.

The transmission control unit 104 receives a set of date-time data and sensor data from the data management unit 102, and determines a reference value to be used for reducing a capacity of the sensor data. More specifically, the transmission control unit 104 may read the reference value from the reference value storage unit 105 if the past reference value is being reused. On the other hand, when the reference value is to be updated, the transmission control unit 104 determines a new reference value as hereinafter described, and stores the determined reference value in the reference value storage unit 105. The reference value storage unit 105 is subjected to read and write operations by the transmission control unit 104 for the reference value.

The transmission control unit 104 calculates a difference between the determined reference value and the biological data (hereinafter referred to as "difference sensor data") and generates a one-way communication packet that stores the difference sensor data. The transmission control unit 104 sends this packet to the transmission unit 106. The transmission unit 106 receives the packet from the transmission control unit 104 and transmits (advertises) the packet.

For example, if the biological data includes values of a systolic blood pressure and a diastolic blood pressure, and if the measurement range of a blood pressure sensor as the biological sensor 101 is 0-299 mmHg, the respective values are represented by 9 bits at most. For practical use, it is sufficient if the range of the systolic blood pressure is set to 44-299 mmHg, and the range of diastolic blood pressure is set to 0-255 mmHg; therefore, the respective values may be represented by 1 byte.

In addition, if the focus is on the short-term blood pressure variation of the same user, the blood pressure variation is assumed to fall within a very small range compared to the entire ranges of the systolic blood pressure and the diastolic blood pressure. If the blood pressure variation of the user is assumed to fall within the range of ±15 mmHg from the median, the systolic blood pressure and the diastolic blood pressure may each be represented by 5 bits; and even if it is assumed to be within the range of ±31 mmHg from the median, each value may be represented by 6 bits. Hence, it is possible to reduce the capacity of the transmission data by transmitting the difference between the reference value and the blood pressure value instead of the blood pressure value itself. The reference value, for example, is preferably a short-term statistical indicator (average value, minimum value, maximum value, median, mode or average of minimum value and maximum value) for the user's blood pressure; however, statistical processing may be omitted by selecting from a plurality of preset reference values.

§ 2 Configuration Example

[Hardware Configuration]
<Data Transmission Apparatus>

Next, an example of a hardware configuration of the data transmission apparatus 100 according to the present embodiment is explained using FIG. 2. FIG. 2 schematically shows an example of a hardware configuration of the data transmission apparatus 100.

As shown in FIG. 2, the data transmission apparatus 100 is a computer in which a controller 111, a storage unit 112, a communication interface 113, an input device 114, an output device 115, an external interface 116 and battery 117 are electrically connected to each other, and its typical implementation is a sensor device for measuring, on a daily basis, an amount related to biological information or active information of a user, such as a blood pressure monitor, a thermometer, an activity monitor, a pedometer, a body composition monitor, or a weight scale. FIG. 2, respectively, describes the communication interface and the external interface as "communication I/F" and "external I/F."

The controller 111 includes CPU (Central Processing Unit), RAM (Random Access Memory), ROM (Read Only Memory), etc. The CPU loads a program stored in the storage unit 112 to the RAM. Further, the CPU interprets and executes this program so that the controller 111 may execute various information processing (processing in each functional block explained in the below section for the functional configuration).

The storage unit 112 is a so-called "auxiliary storage device" which may be, for example, a semiconductor memory such as an embedded or external flash memory, a hard disk drive (HDD), and a solid-state drive (SSD). The storage unit 112 stores a program executed by the controller 111, the data (e.g., reference value, date-time data, and sensor data) used by the controller 111, and so on.

The communication interface 113 at least includes a wireless module capable of one-way communication such as BLE. The input device 114 includes a device for accepting user input, such as, e.g., a touch screen, a button, and a switch, and a sensor for detecting the amount related to the user's biological information and activity information. The output device 115 is a device for performing the output, such as a display, a speaker, or the like.

The external interface 116 is a USB (Universal Serial Bus) port, a memory card slot, etc., and is an interface for connecting with external devices.

The battery 117 supplies power source voltage to the data transmission apparatus 100. The battery 117 may be exchangeable. Further, it is not necessary for the data transmission apparatus 100 to be battery-operated; it may be connected to a commercial power source via an AC (Alternating Current) adapter. In this case, the battery 117 may be omitted.

Further, with regards to the detailed hardware configuration of the data transmission apparatus 100, the omission, substitutions, and addition of the features are suitably possible depending on the embodiment. In an exemplary instance, the controller 111 may include a plurality of processors. The data transmission apparatus 100 may be configured with a plurality of sensor devices.

<Data Reception Apparatus>

Next, an example of a hardware configuration of the data reception apparatus 200 according to the present embodiment is explained using FIG. 3. FIG. 3 schematically shows an example of a hardware configuration of the data reception apparatus 200.

As shown in FIG. 3, the data reception apparatus 200 is a computer, typically a smartphone, in which a controller 211, a storage unit 212, a communication interface 213, an input device 214, an output device 215, and an external interface 216 are electrically connected to each other. FIG. 3, respectively, describes the communication interface and the external interface as "communication I/F" and "external I/F."

The controller 211 includes CPU, RAM, ROM, etc. The CPU loads a program stored in the storage unit 212 to RAM. Further, the CPU interprets and executes this program so that the controller 211 may execute various information processing (processing in each functional block explained in the below section for the functional configuration).

The storage unit 212 is a so-called "auxiliary storage device" which may be, for example, a semiconductor memory such as an embedded or external flash memory. The storage unit 212 stores the program executed by the controller 211, the data (e.g., identifier, reference value, date-time data, and sensor data) used by the controller 211, and so on. Further, if the data reception apparatus 200 is a laptop computer or a desktop computer, the storage unit 212 may be an HDD or SSD.

The communication interface 213 is a communication module for various wireless communication such as mainly BLE, mobile communication (3G, 4G, etc.), and WLAN (Wireless Local Area Network), and is an interface that performs wireless communication via a network. The communication interface 213 may further comprise a wired communication module, such as a wired LAN module.

The input device 214 is a device for accepting user input, such as, e.g., a touch screen, a keyboard, and a mouse. The output device 215 is a device for performing the output, e.g., a display, a speaker or the like.

The external interface 216 is a USB port, a memory card slot or the like, and is an interface for connecting with external devices.

Further, with regards to the detailed hardware configuration of the data reception apparatus 200, the omission, substitution, and addition of the features are suitably possible depending on the embodiment. In an exemplary instance, the controller 211 may include a plurality of processors. The data reception apparatus 200 may be configured with a plurality of information processing devices. Further, the data reception apparatus 200 may be a general-purpose desktop PC (personal computer), tablet PC, etc., or an information processing device designed specifically for the provided service.

[Functional Configuration]

<Data Transmission Apparatus>

Figure 4:
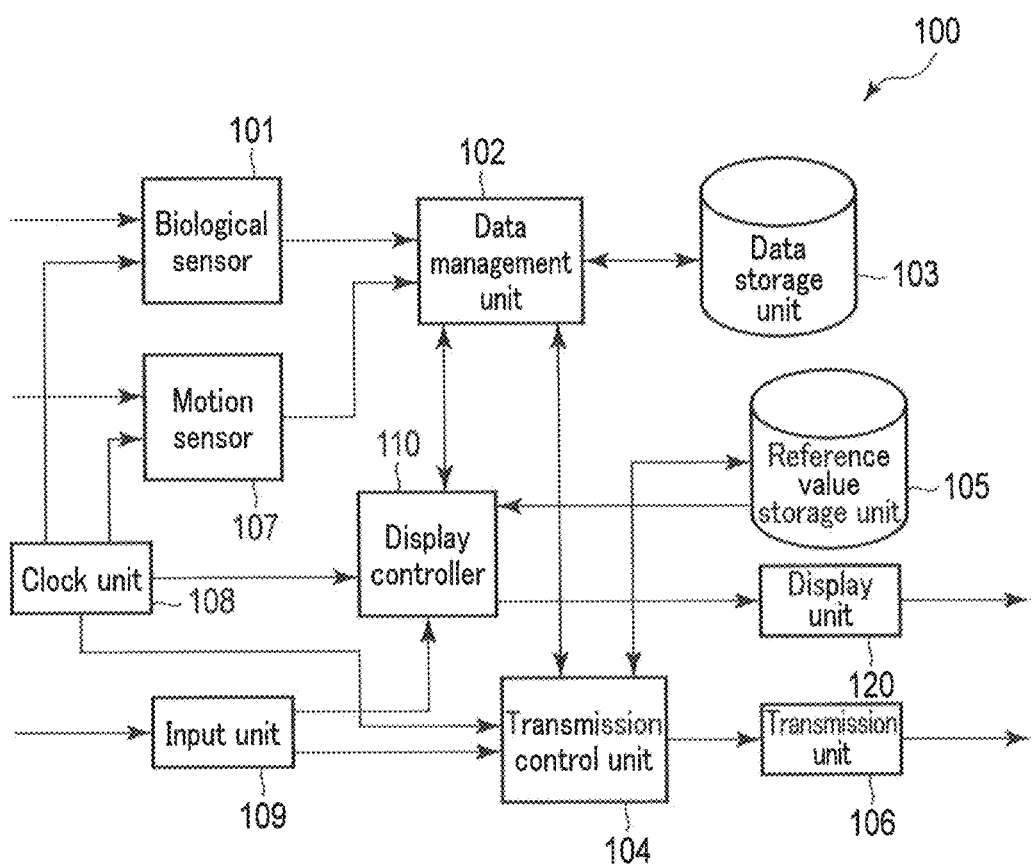
FIG. 4 is a block diagram showing a functional configuration of a data transmission apparatus according to an embodiment.

Next, an example of a functional configuration of the data transmission apparatus 100 according to the present embodiment is explained by using FIG. 4. FIG. 4 schematically shows an example of a functional configuration of the data transmission apparatus 100.

As explained in FIG. 2, the controller 111 loads the program stored in the storage unit 112 to the RAM. Then, the controller 111 interprets and executes, courtesy of the CPU, this program to control various hardware elements shown in FIG. 2. As shown in FIG. 4, the data transmission apparatus 100 thus functions as a computer including the biological sensor 101, the data management unit 102, the data storage unit 103, the transmission control unit 104, the reference value storage unit 105, the transmission unit 106, a motion sensor 107, a clock unit 108, an input unit 109, a display controller 110 and a display unit 120.

The biological sensor 101 obtains biological data by measuring the amount related to the biological information of the user. The operation of the biological sensor 101 is controlled by, for example, a sensor controller (not shown). The biological sensor 101 associates the biological data with date-time data received from the clock unit 108 and sends it to the data management unit 102. The biological sensor 101 typically includes a blood pressure sensor for obtaining blood pressure data by measuring the blood pressure of the user. In this case, the biological data includes the blood pressure data. The blood pressure data may include the values of the systolic blood pressure, the diastolic blood pressure and a pulse rate, but is not limited to the aforementioned. The biological data may include ECG data, pulse wave data, temperature data, or the like.

The blood pressure sensor may include a blood pressure sensor capable of continuously measuring the blood pressure of a user on a beat by beat basis (hereinafter referred to as a "continuous blood pressure sensor"). The continuous blood pressure sensor may continuously measure the blood pressure of a user from a pulse transit time (PTT), but this may be achieved by the tonometry method or other continuous measurement methods.

The blood pressure sensor, instead of, or in addition to, the continuous blood pressure sensor, may include a blood pressure sensor not capable of the continuous measurement (hereinafter referred to as a "non-continuous blood pressure sensor"). The non-continuous blood pressure sensor measures the blood pressure of the user using, for example, a cuff as a pressure sensor (oscillometric method).

The non-continuous blood pressure sensor (in particular, the blood pressure sensor of the oscillometric method) is considered to have high measurement precision compared to the continuous blood pressure sensor. Hence, the blood pressure sensor may measure the blood pressure data with higher precision by operating the non-continuous blood pressure sensor instead of the continuous blood pressure sensor in response to, for example, the satisfaction of some condition (for example, the blood pressure data of the user measured by the continuous blood pressure sensor suggests a predetermined state) as a trigger.

The data management unit 102 receives sensor data (biological data or acceleration/angular velocity data) associated with the date-time data from the biological sensor 101 or motion sensor 107, and writes the data to the data storage unit 103. When the data management unit 102 newly receives the date-time data and sensor data, these may be automatically transmitted to the transmission control unit 104 or display controller 110. Further, the data management unit 102 may be triggered by the instructions from the transmission control unit 104 or display controller 110 so that it reads a set of the date-time data and the sensor data stored in the data storage unit 103, and transmits to the transmission control unit 104 or the display controller 110.

The data storage unit 103 is subjected to read and write operations by the data management unit 102 for the set of the date-time data and the sensor data.

The transmission control unit 104 receives the set of the date-time data and the sensor data from the data management unit 102, and determines a reference value to be used for reducing a capacity of the sensor data. More specifically, the transmission control unit 104 may read the reference value from the reference value storage unit 105 if the past reference value is being reused. On the other hand, when the reference value is being updated, the transmission control unit 104 determines a hereinafter described new reference value and stores the determined reference value in the reference value storage unit 105.

The transmission control unit 104 may update the reference value at a predetermined cycle of, for example, one week, one month or one year, or may update the reference value when a specific user input is provided to the input unit 109 as a trigger. Alternatively, the transmission control unit 104 may determine whether or not to update the reference value based on the statistical indicators for the absolute difference value (average value, minimum value, maximum value, median, mode, or average of minimum value and maximum value, etc.). For example, when the blood pressure of the user shows a tendency that is high or low compared to the past, the reference value is updated to conform to the current tendency of the user to prevent a difference from exceeding the representing capability of the allocated bit number.

The transmission control unit 104 calculates the difference between the determined reference value and sensor data and generates a one-way communication packet which stores the difference sensor data. The transmission control unit 104 sends the generated packet to the transmission unit 106. This packet is, for example, an advertisement packet in BLE. However, the BLE may be replaced with another form of low-power-consumption, one-way communicable communication standard in the future. In such a case, the following explanation may be suitably replaced. The explanation of the BLE advertisement is explained later.

The transmission control unit 104 may receive a user input for controlling data transmission by the transmission unit 106 from the input unit 109. In this case, the transmission control unit 104 requests a set of specific date-time data and sensor data from the data management unit 102 based on the user input and updates the reference value. The transmission control unit 104 may generate an advertisement packet regardless of user input, for retransmission of data transmitted in the past.

The reference value storage unit 105 may be subjected to read and write operations by the transmission control unit 104 for the reference value. Furthermore, the reference value stored in the reference value storage unit 105 may be read by the display controller 110.

The transmission unit 106 receives the BLE advertisement packet from the transmission control unit 104 and transmits (advertises) the packet.

The motion sensor 107, for example, may be an acceleration sensor or a gyrosensor. The motion sensor 107 obtains three-axis acceleration/angular velocity data by detecting the acceleration/angular velocity applied to the motion sensor 107. The operation of the motion sensor 107 is controlled by, for example, a sensor controller (not shown). This acceleration/angular velocity data may be used to estimate an activity status (posture and/or motion) of the user wearing the data transmission apparatus 100. The motion sensor 107 associates the acceleration/angular velocity data with the date-time data received from the clock part 108, and sends it to the data management unit 102.

Further, either one of the biological sensor 101 or the motion sensor 107 may be omitted. Further, an environment sensor may be provided in addition to, or instead of, the biological sensor 101 and motion sensor 107. The environment sensor may include, for example, a temperature sensor, a humidity sensor, an atmospheric pressure sensor, or the like. In other words, the sensor data may be any data generated by a sensor based on a result of its measuring the predetermined physical amount.

The clock unit 108 instructs the date and time. The clock unit 108 includes, for example, a crystal oscillator which vibrates at a fixed frequency, a frequency divider which obtains 1 Hz signals by dividing an output of the crystal oscillator, and a counter for obtaining a serial number showing the date and time by counting the signals. The clock unit 108 transmits date-time data (for example, the above serial number) showing the current date and time to the biological sensor 101 and motion sensor 107. The date-time data may be used as the measurement date and time of the biological data by the biological sensor 101 and the measurement date and time of the acceleration/angular velocity data by the motion sensor 107 etc. Furthermore, the date-time data is referred to by the display controller 110 for display on the display unit 120.

The clock unit 108 (the serial number held by it) may be designed to be, e.g., adjustable by user input (time adjustment); however, the input device 114 may also be simplified (with fewer buttons, etc.) by non-resort to such design. In the latter case, it is still possible to present a user with a relative date and time based on the current date and time, such as, "ten minutes before," "two hours before," "yesterday" and "one week before."

The input unit 109 receives a user input. The user input is for controlling data transmission by the transmission unit 106, for controlling data display by the display unit 120, and for starting measurements by the biological sensor 101 or the motion sensor 107.

The user input for controlling data transmission by the transmission unit 106 takes the form of, for example, explicitly or implicitly instructing transmission of a set of specific date-time data and sensor data and explicitly or implicitly instructing a change of the reference value. As hereinafter described, according to the data configuration of FIG. 8, the reference value also functions as a substantial encryption key; and therefore, the security of the transmission data may be enhanced by actively changing the reference value.

The input unit 109 sends a user input for controlling data transmission by the transmission unit 106 to the transmission control unit 104, sends a user input for controlling data display by the display unit 120 to the display controller 110, and sends a user input for starting measurement by the biological sensor 101 or the motion sensor 107 to the unillustrated sensor controller.

The display controller 110 receives a set of date-time data and sensor data from the data management unit 102 and generates display data for the display unit 120 based on the above. Further, the display controller 110 may refer to the clock unit 108 to generate display data for displaying the date-time data stored by the clock unit 108 on the display unit 120. Further, the display controller 110 refers to the reference value storage unit 105 to generate display data for displaying the reference value on the display unit 120. According to the data configuration of FIG. 8, the reference value functions as a substantial encryption key; thus, the reference value may be set to the data reception apparatus 200 by the user manually inputting the reference value displayed on the display unit 120 to the data reception apparatus 200, without using a wireless transmission which has the risk of being intercepted by a third party. The display controller 110 sends the generated display data to the display unit 120.

The display controller 110 may receive a user input for controlling data display by the display unit 120 from the input unit 109. In this case, the display controller 110 requests a set of specific date-time data and sensor data to the data management unit 102 based on the user input, requests a substantially latest version of date-time data to the clock unit 108 and reads the reference value from the reference value storage unit 105.

The display unit 120 receives and displays the display data from the display controller 110.

The following is a schematic explanation regarding the BLE advertisement.

Figure 5:
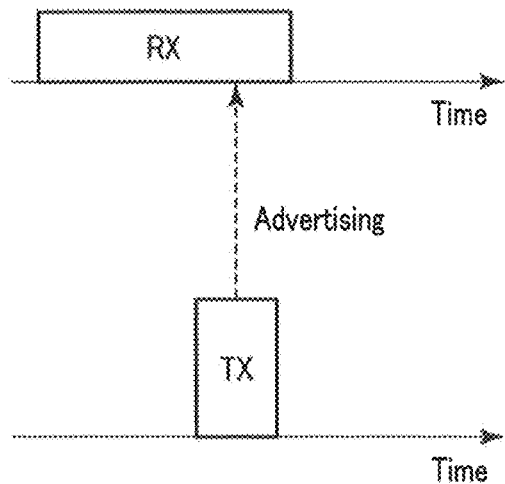
FIG. 5 is a diagram illustrating advertising performed in BLE.

In the passive scanning method adopted by the BLE, as exemplified in FIG. 5, the new node periodically transmits advertisement packets to inform its existence. This new node may reduce power consumption by entering into a sleep state of low power consumption between the times of transmitting an advertisement packet and the next transmission. Furthermore, the reception side of the advertisement packet is also of an intermittent operation; thus, the power consumption for transmission/reception of the advertisement packet is low.

Figure 6:
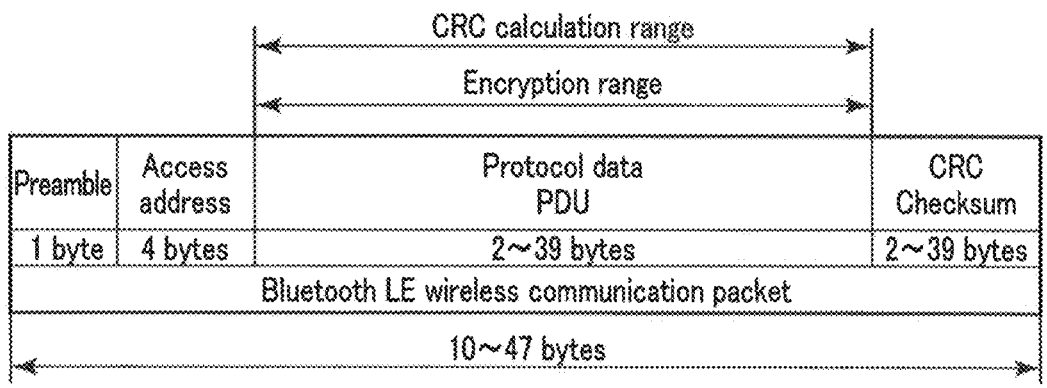
FIG. 6 is a diagram showing a data configuration of a packet transmitted/received in the BLE.

FIG. 6 shows the basic configuration of the BLE wireless communication packet. The BLE wireless communication packet includes a 1-byte preamble, 4-byte access address, 2 to 39-byte (variable) protocol data unit (PDU), and 3-byte cyclic redundancy checksum (CRC). The length of the BLE wireless communication packet is dependent on the length of PDU and is 10-47 bytes. The 10-byte BLE wireless communication packet (PDU is 2 bytes) is called an Empty PDU packet and is periodically exchanged between the master and the slave.

The preamble field is prepared for synchronization of BLE wireless communication, and repetition of "01" or "10" is stored therein. The access address stores fixed numerals for the advertising channel, and stores a random number access address for the data channel. The present embodiment targets an advertisement packet which is the BLE wireless communication packet transmitted on the advertising channel. The CRC field is used to detect a reception error. A calculation range of CRC is only the PDU field.

Figure 7:
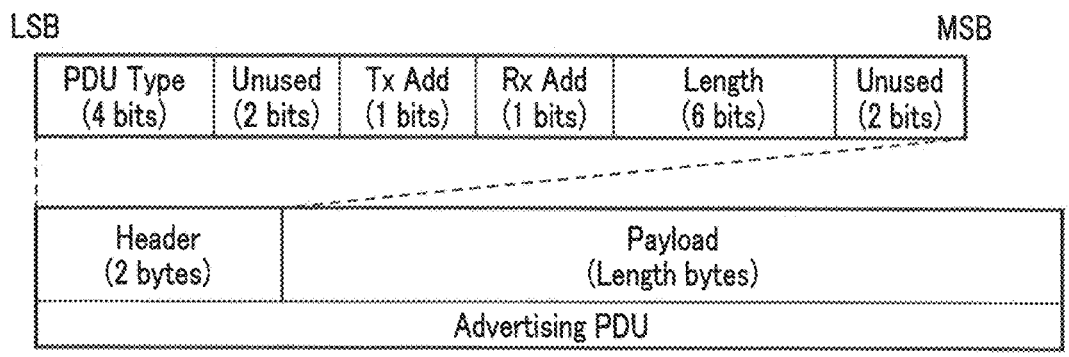
FIG. 7 is a diagram showing a data configuration of a PDU field of an advertisement packet.

Next, FIG. 7 is used to explain the PDU field of the advertisement packet. Note that the PDU field of the data communication packet, which is the BLE wireless communication packet transmitted on the data channel, has a data configuration different from FIG. 7; however, the present embodiment does not target the data communication packet, and the explanation will thus be omitted.

The PDU field of an advertisement packet includes a 2-byte header and a 0 to 37-byte (variable) payload. The header further includes a 4-bit PDU type field, 2-bit unused field, 1-bit TxAdd field, 1-bit RxAdd field, 6-bit Length field, and 2-bit unused field.

The PDU type field stores a value indicating a type of this PDU. Various values, such as the "connectible advertising" and "non-connectible advertising," are already defined. The TxAdd field stores a flag indicating whether or not there is a transmission address in the payload. Similarly, the RxAdd field stores a flag indicating whether or not there is a reception address in the payload. The Length field stores a value indicating the byte size of the payload.

The payload can store desired data. The data transmission apparatus 100 uses the data configuration exemplified in, for example, FIG. 8, 9, 10 or 14 to store the difference sensor data and the date-time data to the payload.

The data configuration of FIG. 8 may be used for transmission of one set's worth of sensor data for blood pressure and pulse rate of one user. Furthermore, the data configuration of FIG. 8 may be modified to transmit multiple sets' worth of sensor data.

The ID field stores an identifier showing a user. Instead of the identifier showing the user, or in addition to such, the identifier showing data transmission apparatus 100 or data reception apparatus 200 may be stored.

The Time field stores the date-time data. DifSys, DifDia, and DifPulse fields respectively store the difference sensor data of the systolic blood pressure, that of the diastolic blood pressure, and that of the pulse rate, associated with the date-time data. The difference sensor data associated with the date-time data is not limited to one type and may be a plurality of types as above.

According to the data configuration of FIG. 8, the reference value used for generating the difference sensor data is not stored in the same packet as the difference sensor data. Thus, even if a third party intercepts this packet having the data configuration of FIG. 8, the original sensor data may not be restored as long as the third party does not know the reference value. In other words, according to the data configuration of FIG. 8, the sensor data may be securely transmitted by substantial encryption. In contrast, when the data reception apparatus 200 cannot specify the reference value, the original sensor data also cannot be restored by the data reception apparatus 200. Thus, the data transmission apparatus 100 may be controlled so that it transmits the reference value upon some type of trigger, for example, a specific user input. The reference value, for example, may be transmitted separately from the difference sensor data by the data transmission apparatus 100, and may set to a value identifiable by the data reception apparatus 200 alone, such as the average value, minimum value, maximum value, median, mode, or the average of the minimum and maximum value of the sensor data for the past week. Alternatively, the reference value may be directly specified by the user input.

The data configuration of FIG. 9 may be used for transmission of one set's worth of sensor data for blood pressure and pulse rate of one user. Furthermore, the data configuration of FIG. 9 may be modified to transmit multiple sets' worth of sensor data. The ID field, Time field, DifSys field, DifDia field and DifPulse field of FIG. 9 are similar to FIG. 8.

The Baseline field stores an identifier showing the reference value used to generate difference sensor data. This identifier shows whether any of a plurality of preset reference values is used to generate the difference sensor data. For example, the preset reference value may be prepared with four types which are: one for severely-high blood pressure users, one for lightly-high blood pressure users, one for average blood pressure users, and one for low blood pressure users. In this case, the identifier may be represented by two bits. However, the preset reference value is not limited to such and may be three types or fewer, or five types or more.

According to the data configuration of FIG. 9, an identifier showing a reference value used for generating difference sensor data is stored in the same packet as the difference sensor data. Hence, according to the data configuration of FIG. 9, the data reception apparatus 200 uses correspondence between the identifiers and the preset reference values, set during initial setting, such as installation of the biological data management application, authentication of the data transmission apparatus 100 or during other updates, to specify the preset reference value indicated by the identifier stored in the packet and to reliably restore the sensor data. On the other hand, even if the third party intercepts the packet having the data configuration of FIG. 9, the original sensor data may not be restored as long as the third party does not know the correspondence between the identifiers and the preset reference values. In other words, the sensor data may be securely transmitted by substantial encryption. Further, the preset reference value shown by each identifier may be randomized by adding different offsets for respective users, instead of being fixed for all users, to increase security by making searches for the correspondence between the identifiers and the preset reference values more difficult for the third party. Alternatively, the correspondence between the identifiers and the preset reference values may be randomized for each user, e.g., shuffled, instead of being fixed for all users.

The data configuration of FIG. 10 may be used for transmitting multiple sets' worth of sensor data for blood pressure and pulse rate of a single user. The ID field of FIG. 10 is similar to FIGS. 8 and 9. According to the data configuration of FIG. 10, for example, the statistical indicator (for example, average value, minimum value, maximum value, median, mode or the average of the minimum value and the maximum value etc.) for a plurality of sets of sensor data, which is to be stored in the same packet, is used as the reference value to generate the difference sensor data based on each sensor data. In other words, the packet stores a common reference value and a plurality of sets of difference sensor data.

The Baseline field stores the reference value. This reference value may be the statistical indicator for a plurality of sets of sensor data and stored in the same packet as described above. More specifically, the Baseline field may include a BSys field, BDia field, and BPulse field.

The BSys field, BDia field, and BPulse field each store the reference value for respective one of the systolic blood pressure, diastolic blood pressure, and pulse rate.

The Time1 field stores the date-time data showing the measurement date and time of a first set of sensor data. The DifSys1 field, DifDia1 field, and DifPulse1 field respectively store the difference sensor data of the systolic blood pressure, that of the diastolic blood pressure, and that of the pulse rate, associated with the date-time data stored in the Time1 field.

The Time2 field stores the date-time data showing the measurement date and time of a second set of sensor data. The DifSys2 field, DifDia2 field, and DifPulse2 field respectively store the difference sensor data of the systolic blood pressure, that of the diastolic blood pressure, and that of the pulse rate, associated with the date-time data stored in the Time2 field.

When storing a third set of sensor data or more into a packet, the Time field, DifSys field, DifDia field, and DifPulse field may be added as necessary.

According to the data configuration of FIG. 10, the reference value itself is stored in the same packet as the difference sensor data generated using the reference value.

Thus, the data reception apparatus 200 may reliably restore the sensor data. On the other hand, when a third party intercepts the packet having the data configuration of FIG. 10, it is necessary to note that this third party may be able to restore the original sensor data.

In the data configuration of FIG. 10, the packet capacity may be efficiently reduced by increasing the number of sets of sensor data stored in the packet. More specifically, let us assume that five sets of sensor data shown in FIG. 11 are stored in a packet. Also, the reference value is assumed to be set to a minimum value of each type of sensor data.

In the example of FIG. 11, the minimum values of the systolic blood pressure, diastolic blood pressure, and pulse rate are "105", "72" and "60", respectively. When these reference values are used, the sensor data may be converted into the difference sensor data exemplified in FIG. 12.

8 bits at most are needed to represent the systolic blood pressure, the diastolic blood pressure, and the pulse rate shown in FIG. 11, while the systolic blood pressure difference, the diastolic blood pressure difference, and the pulse rate difference shown in FIG. 12 may be represented by 5 bits at most. When the systolic blood pressure, the diastolic blood pressure and the pulse rate are each allocated with 8 bits, 120 bits (8*3*5) are needed to transmit the five sets' worth of original sensor data. On the other hand, when 5 bits are allocated to each of the systolic blood pressure difference, the diastolic blood pressure difference, and the pulse rate difference, the data amount needed will be only 99 bits, even if the five sets' worth of the difference sensor data is sent together with the reference values (5*3*5+8*3). Hence, 18% data reduction (smaller capacity) has been rendered possible for the sensor data and the reference values. As exemplified in FIG. 13, the data reduction rate improves as more sets of sensor data are stored in the same packet.

Figure 14:
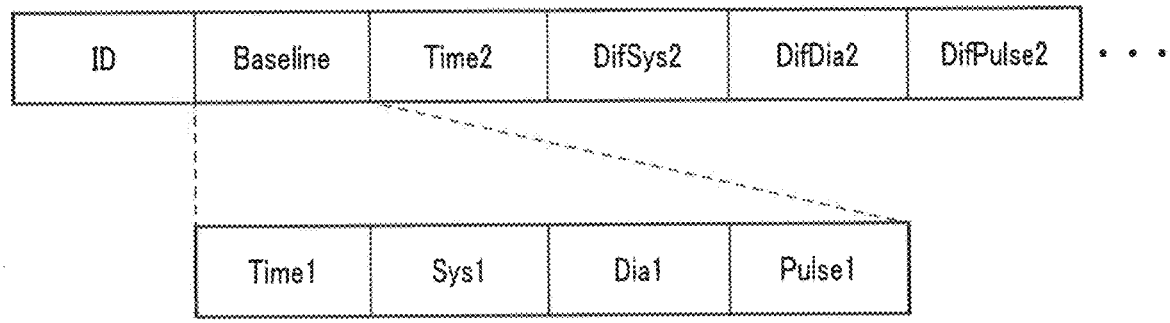
FIG. 14 is a diagram showing a fourth example of a data configuration for storage in a payload of a PDU field of a packet transmitted by a data transmission apparatus according to an embodiment.

The data configuration of FIG. 14 may be used for transmitting multiple sets' worth of sensor data for blood pressure and pulse rate of a single user. The ID field of FIG. 14 is similar to FIGS. 8, 9, and 10. According to the data configuration of FIG. 14, any one set of sensor data, data configuration of FIG. 14, any one set of sensor data, e.g., a first set of sensor data, is used as a reference value to generate the difference sensor data based on other sensor data. In other words, the packet stores the first set of sensor data as a reference value and difference sensor data of the second set and onwards.

The Baseline field stores the reference value. As described, this reference value is the first set of sensor data. More specifically, the Baseline field may include a Time1 field, Sys1 field, Dial field, and Pulse1 field.

The Time1 field stores the date-time data showing the measurement date and time of the first set of sensor data. The Sys1 field, Dial field, and Pulse1 field respectively store the systolic blood pressure, the diastolic blood pressure, and the pulse rate, associated with the date-time data stored in the Time1 field.

The Time2 field stores the date-time data showing the measurement date and time of the second set of sensor data. The DifSys2 field, DifDia2 field, and DifPulse2 field respectively store the difference sensor data of the systolic blood pressure, that of the diastolic blood pressure, and that of the pulse rate, associated with the date-time data stored in the Time2 field.

When storing the third set of sensor data or more into a packet, the Time field, DifSys field, DifDia field, and DifPulse filed may be added as necessary.

Similar to the data configuration of FIG. 10, according to the data configuration of FIG. 14, the reference value itself is stored in the same packet as the difference sensor data generated using the reference value. Thus, the data reception apparatus 200 may reliably restore the sensor data. On the other hand, when the packet having the data configuration of FIG. 14 is intercepted by a third party, it is necessary to note that this third party may be able to restore the original sensor data. Furthermore, according to the data configuration of FIG. 14, since any one set of sensor data is used as the reference value, it is possible to reduce the capacity by one set's worth of difference sensor data compared to the data configuration of FIG. 10.

<Data Reception Apparatus>

Figure 15:
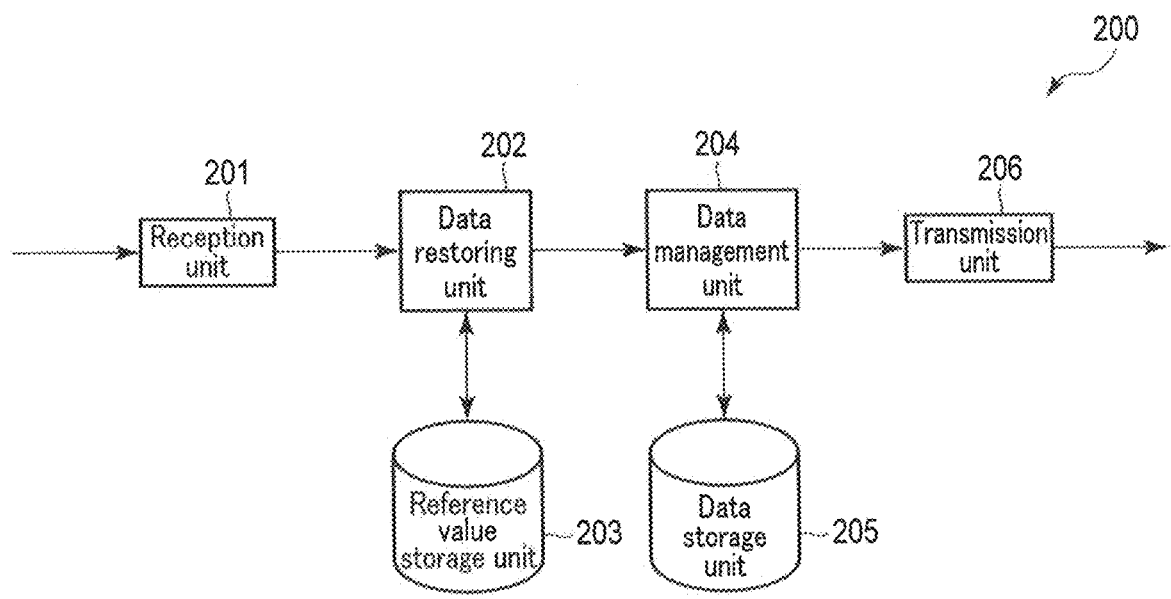
FIG. 15 is a block diagram showing a functional configuration of a data reception apparatus according to an embodiment.

Next, an example of a functional configuration of the data reception apparatus 200 according to the present embodiment is explained using FIG. 15. FIG. 15 schematically shows an example of a functional configuration of the data reception apparatus 200.

As explained in FIG. 3, the controller 211 loads a program stored in the storage unit 212 to RAM. Then, the controller 211, courtesy of the CPU, interprets and executes this program to control various hardware elements shown in FIG. 3. As shown in FIG. 15, the data reception apparatus 200 thus functions as a computer including a reception unit 201, a data restoring unit 202, a reference value storage unit 203, a data management unit 204, a data storage unit 205, and a transmission unit 206.

The reception unit 201 receives a packet including sensor data and date-time data associated with the sensor data from the data transmission apparatus 100. The reception unit 201, for example, extracts a PDU payload from the BLE advertisement packet. Further, the reception unit 201 may discard a received packet if the value in the ID field is unsuitable (for example, it does not match with the value that shows the own user). On the other hand, the reception unit 201 transmits other various data to the data restoring unit 202 if the value in the ID field is suitable (for example, it matches with the value that shows the own user).

In the example of the data configuration of FIG. 8, the reception unit 201 sends the date-time data stored in the Time field and the difference sensor data stored in the DifSys field, DifDia field, and DifPulse field to the data restoring unit 202.

In the example of the data configuration of FIG. 9, the reception unit 201 sends the date-time data stored in the Time field, the identifier showing the reference value and stored in the Baseline field, and the difference sensor data stored in the DifSys field, DifDia field and DifPulse field to the data restoring unit 202.

In the example of data configuration of FIG. 10, the reception unit 201 sends the reference values stored in the BSys field, BDia field, and Bpulse field; the date-time data associated with the first set of difference sensor data and stored in the Time1 field; the first set of difference sensor data stored in the DifSys1 field, DifDia1 field, and DifPulse1 field; the date-time data associated with the second set of difference sensor data and stored in the Time2 field; and the second set of difference sensor data stored in the DifSys2 field, DifDia2 field, and DifPulse2 field to the data restoring unit 202.

In the example of the data configuration of FIG. 14, the reception unit 201 sends, to the data restoring unit 202, the date-time data associated with the first set of sensor data stored in the Time1 field; the first set of sensor data stored in the Sys1 field, Dia1 field, and Pulse1 field as the reference value; the date-time data associated with the second set of difference sensor data stored in the Time2 field; and the second set of difference sensor data stored in the DifSys2 field, DifDia2 field, and DifPulse2 field.

The data restoring unit 202 receives various data, including the difference sensor data from the reception unit 201. The data restoring unit 202 determines the reference value for restoring the original sensor data from the difference sensor data. How the data restoring unit 202 determines the reference value is dependent on the data configuration of the packet.

When the packet has the data configuration of FIG. 8, the reference value used for generating the difference sensor data is not stored in the same packet as the difference sensor data. Hence, the data restoring unit 202 may not receive the difference sensor data and the reference value from the reception unit 201 at the same time. The reference value may be: directly stored in the reception data other than the packet and provided to the data restoring unit 202; specified based on the reception data; specified by user input; or already saved at the reference value storage unit 203. The data restoring unit 202 determines the reference value based on reception data or user input when the reference value is not stored in the reference value storage unit 203 or when the reference value cannot be reused. If there is a possibility that the determined reference value will be reused, the data restoring unit 202 may store the reference value in the reference value storage unit 203.

When the packet has the data configuration exemplified in FIG. 9, the data restoring unit 202 receives the identifier showing the reference value and stored in the Baseline field from the reception unit 201. The data restoring unit 202 can specify the reference value by reading one of the plurality of preset reference values stored in the reference value storage unit 203, indicated by the identifier.

When the packet has the data configuration exemplified in FIG. 10, the data restoring unit 202 receives the reference values stored in the BSys field, BDia field, and BPulse field from the reception unit 201. Hence, the data restoring unit 202 may use these reference values.

When the packet has the data configuration exemplified in FIG. 14, the data restoring unit 202 receives the first set of sensor data as the reference values stored in the Sys1 field, Dia1 field, and Pulse1 field from the reception unit 201. Hence, the data restoring unit 202 may use these reference values.

The data restoring unit 202 restores the sensor data corresponding to the difference sensor data by adding the difference sensor data to the determined reference value, regardless of the data configuration of the packet. The data restoring unit 202 sends the restored sensor data to the data management unit 204 along with the date-time data received from the reception unit 201.

The reference value storage unit 203 may be subjected to read and write operations by the data restoring unit 202 for the reference values. The reference value storage unit 203 may store preset reference values used for the data configuration of FIG. 9. Further, when the reference value is only applied once as in the data configurations of FIGS. 10 and 14, the reference value storage unit 203 may be omitted since there is no need to store the reference value.

The data management unit 204 receives the date-time data and the sensor data from the data restoring unit 202, associates them together, and writes them in the data storage unit 205. The data management unit 204 reads a set of the date-time data and the sensor data stored in the data storage unit 205 in accordance with the instruction from, e.g., an upper application (not shown), for example a management application for biological data, and transmits the read set to the transmission unit 206 or an unillustrated display unit.

The data storage unit 205 may be subjected to read and write operations by the data management unit 204 for the set of the date-time data and the sensor data.

Figure 16:
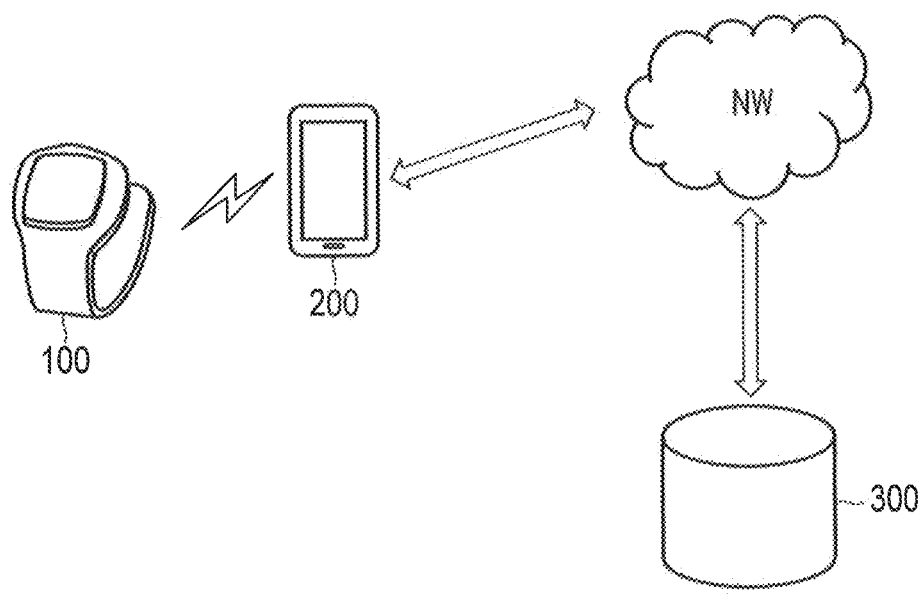
FIG. 16 is a diagram showing a data transmission system including a data transmission apparatus and a data reception apparatus according to an embodiment.

The transmission unit 206 receives the set of date-time data and a sensor data from the data management unit 204 and transmits it to a server 300 via a network (refer to FIG. 16). The transmission unit 206 uses, for example, mobile communication or WLAN. Note that the example of FIG. 16 shows the exterior of a wristwatch-type wearable blood pressure monitor as the data transmission apparatus 100; however, the exterior of the data transmission apparatus 100 is not limited to the above and may be a stationary blood pressure monitor or a sensor device for measuring the amount related to other biological information or activity information.

The server 300 corresponds to a database which manages sensor data (mainly, biological data) of various users. The server 300 may transmit biological data of the user, in response to access from the user's personal computer, as well as from, for example, a wellness advisor's, an insurance company's or program operator's PC, etc., to provide health guidance for the user, insurance coverage assessment, and health promotion program evaluation, etc.

<Others>

The details regarding each function of the data transmission apparatus 100 and data reception apparatus 200 will be explained in the operation example below. The present embodiment has assumed the instances where the general-purpose CPU is employed to realize each function of the data transmission apparatus 100 and data reception apparatus 200. However, a part of or the whole of the discussed functions may be realized by one or a plurality of dedicated processors. Moreover, with regards to the functional configurations of the respective data transmission apparatus 100 and data reception apparatus 200, the omission, substitution, and addition of functions are suitably possible depending on the implementations.

§ 3 Example of Operation

<Data Transmission Apparatus>

Figure 17:
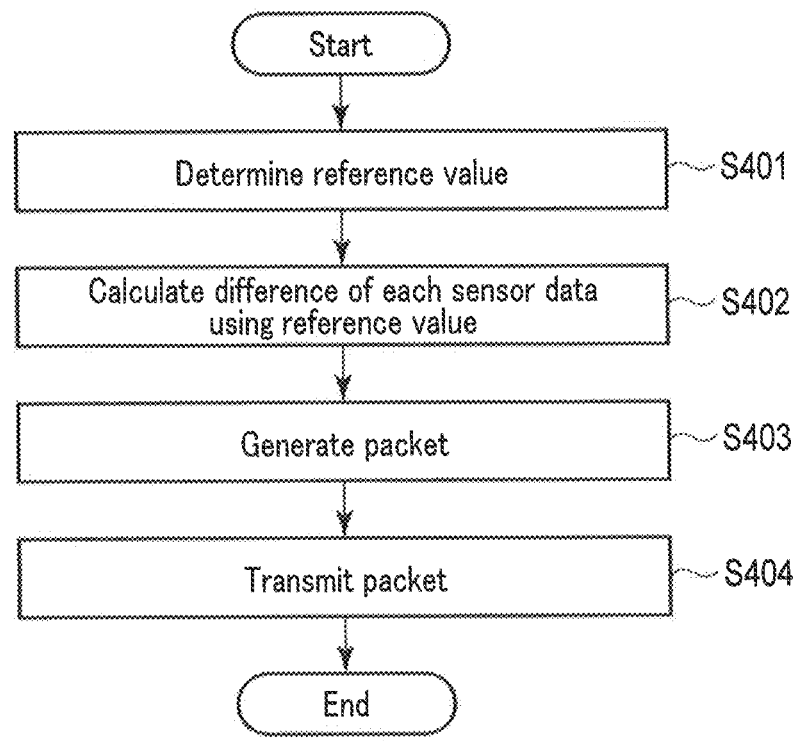
FIG. 17 is a flowchart showing an operation of a data transmission apparatus according to an embodiment.

Next, an example of an operation of the data transmission apparatus 100 is explained by referring to FIG. 17. FIG. 17 is a flowchart showing an example of the operation of the data transmission apparatus 100. The hereinafter described process is merely an example, and the process may be changed as much as possible. The omission, substitution, and addition of steps in the following process are possible as appropriate depending on the implementations.

The operation example of FIG. 17 starts with the transmission control unit 104 receiving a set of date-time data and sensor data from the data management unit 102, for transmitting to the data reception apparatus 200.

The transmission control unit 104 determines a reference value associated with the sensor data, which is a transmission object (step S401). More specifically, the transmission control unit 104 may read the reference value from the reference value storage unit 105 if the past reference value is being reused. On the other hand, when the reference value is being updated, the transmission control unit 104 determines a new reference value as hereinafter described, and stores the determined reference value in the reference value storage unit 105.

The transmission control unit 104 calculates difference sensor data, which is a difference between the reference value determined in step S401 and the sensor data (step S402). Further, the transmission control unit 104 generates a packet for one-way communication which stores the difference sensor data calculated in step S402 and the date-time data (step S403). The data configuration exemplified in FIG. 8, 9, 10, or 14 may be useful for the generation of a packet; however, other data configuration may be utilized.

The transmission unit 106 transmits the packet generated in step S403 (step S404), and the process is finished.

<Data Reception Apparatus>

Figure 18:
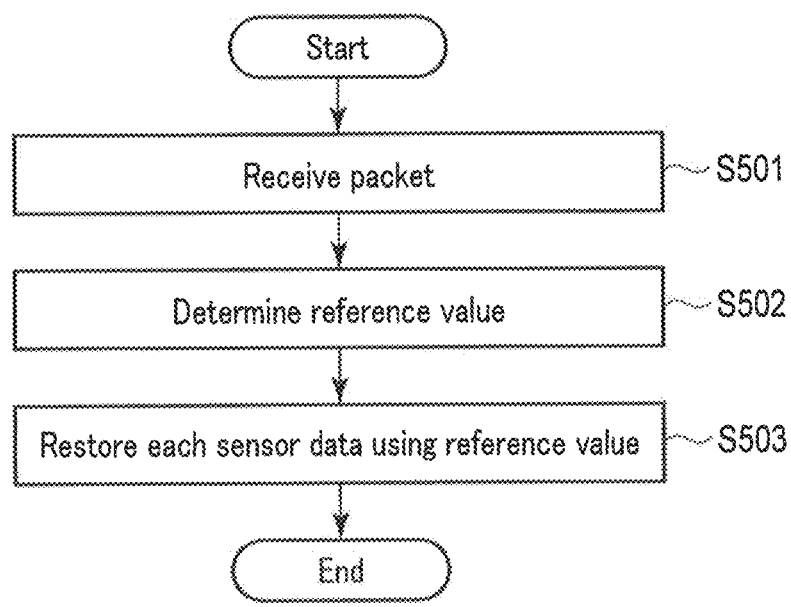
FIG. 18 is a flowchart showing an operation of a data reception apparatus according to an embodiment.

Next, an example of an operation of the data reception apparatus 200 is explained with reference to FIG. 18. FIG. 18 is a flowchart showing an example of the operation of the data reception apparatus 200. The following process is merely an example, and the process may be changed as much as possible. The omission, substitution, and addition of steps in the hereinafter described process are possible as appropriate depending on the implementations.

FIG. 18 shows the operation example up to restoring the original sensor data from the difference sensor data stored in a packet transmitted by the data transmission apparatus 100. The data reception apparatus 200 repeatedly conducts the operation example of FIG. 18 for each packet.

Firstly, the reception unit 201 receives the packet and extracts the difference sensor data stored in the packet (step S501). The data restoring unit 202 determines the reference value for restoring the original sensor data from the difference sensor data extracted in step S501 (step S502). As mentioned above, the way in which the data restoring unit 202 determines the reference value is dependent on the data configuration of the packet.

The data restoring unit 202 adds the difference sensor data extracted in step S501 to the reference value determined in step S502 to restore the sensor data corresponding to the difference sensor data (step S503). The process ends with this step S503.

Advantageous Effects

As explained above, in the present embodiment, the data transmission apparatus determines a reference value associated with sensor data and calculates difference sensor data, which is the difference between this reference value and the sensor data. Further, the data transmission apparatus stores the difference sensor data instead of the sensor data into a one-way communication packet and sends it to the data reception apparatus. Then, the data reception apparatus determines the reference value associated with the difference sensor data stored in the packet and restores the original sensor data by combining the reference value and the difference sensor data. Typically, it is rare for the blood pressure of the same person to drastically change over a short period; thus, the number of bits allocated for transmission of the difference sensor data may be limited compared to the number of bits allocated for transmission of raw sensor data. Hence, according to the data transmission apparatus and data reception apparatus, the capacity of the packet transmitted by the one-way communication may be reduced.

In addition, as exemplified in FIG. 8 or 9, the sensor data may be substantially encrypted and securely sent by not storing the information clearly indicating the reference value used for calculation of the difference sensor data in the same packet that stores the difference sensor data.

§ 4 Modifications

Although the embodiment of the present invention has been described in detail in the foregoing, the description is merely an example of the present invention in every respects. Various improvements and modifications can, of course, be made to the embodiment without deviating from the scope of the present invention. The following modifications may be made for example. In the following, the same reference numerals are used for the same constituent elements of the foregoing embodiment, and redundant descriptions are omitted as appropriate. The following modifications may be combined as appropriate.

<4.1>

In an exemplary instance, in the above embodiment, the data transmission apparatus enhances transmission efficiency by transmitting a packet, including difference sensor data instead of the sensor data. However, though it is rare that biological information such as blood pressure of the same person drastically changes over a short period, the data size of the difference sensor data may become larger than that of the sensor data. Thus, for example, when the data size of the difference sensor data is larger than that of the raw sensor data, the transmission control unit generates a second packet for one-way communication including the sensor data, instead of generating the first packet including the difference sensor data, and the transmission unit may transmit the second packet. Furthermore, to determine which of the first packet or the second packet was received at the data reception apparatus, the transmission control unit may include information showing the packet type in each of the first packet and the second packet. According to the modified example, the effect of reducing capacity by transmitting the packet including the difference sensor data instead of the sensor data may be undoubtedly achieved.

However, the above-explained modification is only an example of the present invention in all aspects. Various improvements and modifications can, of course, be made to it without deviating from the scope of the present invention. Thus, when the present invention is implemented, a detailed structure depending on the implementations may be suitably adopted. Further, the data introduced in each embodiment has been explained by natural language; however, more specifically, the data items are specified by pseudolanguage, commands, parameters, machine language etc. recognized by a computer.

§ 5 Additional Note

A part of or all of each embodiment above may also be described as in the following additional notes, aside from the scope of claims, without limitation thereto.

(Additional Note 1)
A data transmission apparatus comprising:
a memory; and
a processor connected to the memory;
wherein the processor is configured to function as:
(a) a transmission control unit which generates a first packet for one-way communication including first difference sensor data; and
(b) a transmission unit which transmits the generated first packet, and
the first difference sensor data is a difference between first sensor data measured by a sensor and a reference value associated with the first sensor data.

(Additional Note 2)
A data reception apparatus comprising:
a memory; and
a processor connected to the memory,
wherein the processor is configured to function as:
(a) a reception unit which receives a first packet for one-way communication including first difference sensor data; and
(b) a restoring unit which restores first sensor data, which is a base of the first difference sensor data, by adding a reference value associated with the first difference sensor data to the first difference sensor data included in the received first packet, and
the first difference sensor data is a difference between the first sensor data and the reference value.

REFERENCE SIGNS LIST

100 . . . Data transmission apparatus
101 . . . Biological sensor
102, 204 . . . Data management unit
103, 205 . . . Data storage unit
104 . . . Transmission control unit
105, 203 . . . Reference value storage unit
106, 206 . . . Transmission unit
107 . . . Motion sensor
108 . . . Clock unit
109 . . . Input unit
111, 211 . . . Controller
112, 212 . . . Storage unit
113, 213 . . . Communication interface
114, 214 . . . Input device
115, 215 . . . Output device
116, 216 . . . External interface
117 . . . Battery
120 . . . Display unit
200 . . . Data reception apparatus
201 . . . Reception unit
202 . . . Data restoring unit
300 . . . Server

The invention claimed is:

1. A data transmission apparatus which communicates with a data reception apparatus, the data transmission apparatus comprising:
a memory; and
a processor connected to the memory,
wherein the processor is configured to:
generate a first packet for one-way communication including first difference sensor data; and
transmit the generated first packet,
the first difference sensor data is a difference between first sensor data measured by a sensor and a reference value associated with the first sensor data,
the processor is configured to generate the first packet to further include an identifier indicative of the reference value being one of a plurality of preset reference values, and
a correspondence between the preset reference values and identifiers is set to the data reception apparatus during initial setting of the data reception apparatus.

2. The data transmission apparatus according to claim 1, wherein the processor is configured to generate the first packet to further include second difference sensor data, and the second difference sensor data is a difference between second sensor data and the reference value, the second sensor data being measured by the sensor and different from the first sensor data.

3. The data transmission apparatus according to claim 1, wherein the processor is configured to generate a second packet for one-way communication including the first sensor data, instead of generating the first packet when a data size of the first difference sensor data is larger than a data size of the first sensor data, and the processor is configured to transmit the generated second packet.

4. The data transmission apparatus according to claim 1, wherein the first sensor data is biological data.

5. A data reception apparatus which communicates with a data transmission apparatus, the data reception apparatus comprising:

a memory; and a processor connected to the memory, wherein the memory is configured to store a plurality of preset reference values, the processor is configured to:

receive a first packet for one-way communication, the first packet including first difference sensor data and an identifier indicative of a reference value associated with the first difference sensor data being one of the preset reference values; and restore first sensor data, which is a base of the first difference sensor data, by selecting a preset reference value indicated by the identifier included in the received first packet from the preset reference values and adding the first difference sensor data included in the received first packet to the selected preset reference value, the first difference sensor data is a difference between the first sensor data and the reference value, and a correspondence between the preset reference values and identifiers is set to the data reception apparatus during initial setting of the data reception apparatus.

6. The data reception apparatus according to claim 5, wherein the first packet further includes second difference sensor data, the processor is configured to restore second sensor data, which is a base of the second difference sensor data, by adding the second difference sensor data included in the received first packet to the reference value, and the second difference sensor data is a difference between the second sensor data and the reference value.

7. The data reception apparatus according to claim 5, wherein the first sensor data is biological data.

\* \* \* \* \*